(12) United States Patent
Toppan (10) Patent No.: US 10,591,629 B2
(45) Date of Patent: Mar. 17, 2020

(54) MOBILE X-RAY SCAN SPEED CONTROL

(71) Applicant: American Science and Engineering, Inc., Billerica, MA (US)

(72) Inventor: Jason Toppan, Burlington, MA (US)

(73) Assignee: American Science and Engineering, Inc., Billerica, MA (US)

(*) Notice: Subject to any disclaimer, the term of this patent is extended or adjusted under 35 U.S.C. 154(b) by 84 days.

(21) Appl. No.: 15/773,888

(22) PCT Filed: Oct. 20, 2016

(86) PCT No.: PCT/US2016/057831
§ 371 (c)(1),
(2) Date: May 4, 2018

(87) PCT Pub. No.: WO2017/083073
PCT Pub. Date: May 18, 2017

(65) Prior Publication Data
US 2018/0329107 A1   Nov. 15, 2018

Related U.S. Application Data

(60) Provisional application No. 62/252,843, filed on Nov. 9, 2015.

(51) Int. Cl.
| G01V 5/00 | (2006.01) |
| G01N 23/02 | (2006.01) |
| G01N 23/083 | (2018.01) |
| G01N 23/222 | (2006.01) |

(52) U.S. Cl.
CPC ........... *G01V 5/0066* (2013.01); *G01N 23/02* (2013.01); *G01N 23/083* (2013.01); *G01N 23/222* (2013.01); *G01V 5/0008* (2013.01)

(58) Field of Classification Search
CPC .... G01N 23/222; G01N 23/02; G01N 23/083; G01V 5/0008; G01V 5/0066
See application file for complete search history.

(56) References Cited

U.S. PATENT DOCUMENTS 5,692,028 A * 11/1997 Geus ................... G01V 5/0008
378/196
5,838,759 A * 11/1998 Armistead ............ B66C 19/007
378/57
6,763,635 B1 * 7/2004 Lowman ............... B60P 1/5433
378/198

FOREIGN PATENT DOCUMENTS

| CN | 1343881 A | 4/2002 |
| CN | 103026214 A | 4/2013 |
| KR | 20140123996 A | 10/2014 |
| WO | 2011137504 A1 | 11/2011 |

OTHER PUBLICATIONS

International Search Report for PCT/US2016/057831, dated Jan. 31, 2017.

* cited by examiner

*Primary Examiner* — Mark R Gaworecki
(74) *Attorney, Agent, or Firm* — Novel IP (57) ABSTRACT

A conveyance and methods for x-ray inspection of an object. The conveyance has a bed with attached wheels and detector elements disposed along a pontine structure coupled to the conveyance. A source of penetrating radiation is coupled to the conveyance and disposed so as to irradiate each of the detector elements from a single position. An automated manual transmission couples power from an engine to a set of the wheels of the conveyance, both for road travel and for x-ray inspection.

30 Claims, 6 Drawing Sheets

MOBILE X-RAY SCAN SPEED CONTROL

CROSS REFERENCE

The present application is a 371 National Stage application of PCT/US2016/057831, entitled "Mobile X-Ray Scan Speed Control" and filed on Oct. 20, 2016, which claims the priority of U.S. Provisional Patent Application 62/252,843, filed Nov. 9, 2015, both of which are incorporated herein by reference in their entirety.

TECHNICAL FIELD

The present invention relates to systems and methods for inspection of cargo using penetrating radiation, and, more particularly to rapidly relocatable, self-propelled systems.

BACKGROUND OF THE INVENTION

Multiple views of a prior art x-ray inspection system, to which the present invention may usefully be applied, are depicted in FIGS. 1A-1D. All systems for security inspection from a moving platform inspecting a vehicle using x-rays transmitted through an inspected vehicle have either required a fixed portal or gantry, or else have employed a ponderous boom or other deployment mechanism, either of which requires a specially designed vehicle for carrying such a mechanism to each inspection venue. Salient components of such mobile inspection systems are described with reference to the numerals designated in FIGS. 1A and 1B. In prior art mobile x-ray inspection system 100, a plurality of detector modules 102 are arrayed in a pontine detector array 104. Detector elements that comprise each of the modules 102 receive radiation directed from an x-ray source 106.

Figure 1A:
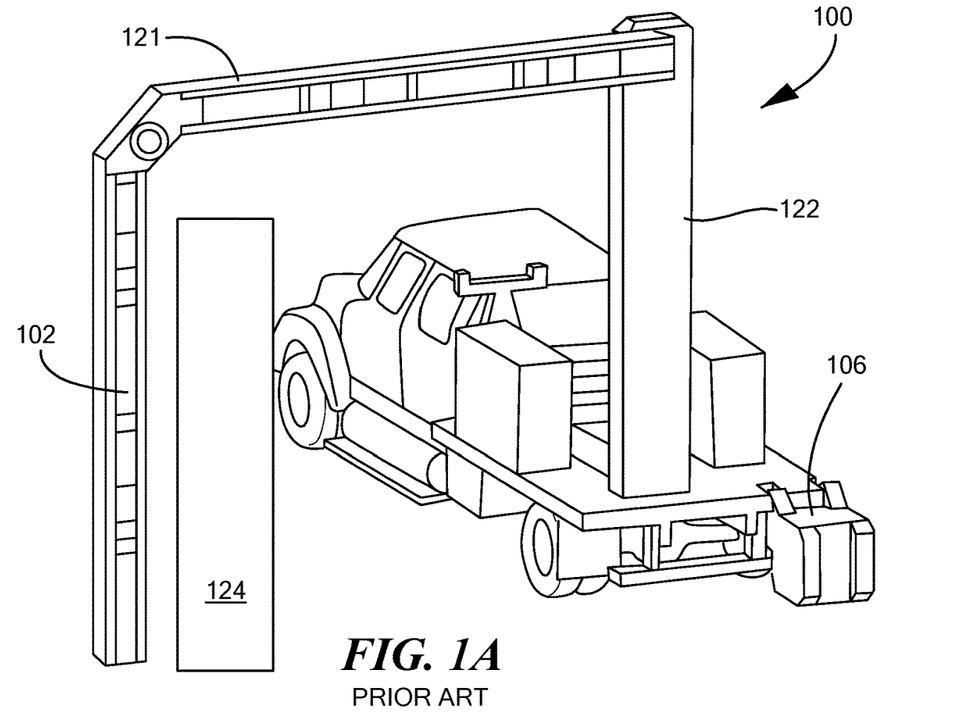
FIGS. 1A-1D depict a prior art X-ray vehicle employed for mobile x-ray inspection, of the sort to which the present invention may be advantageously applied.
Figure 1B:
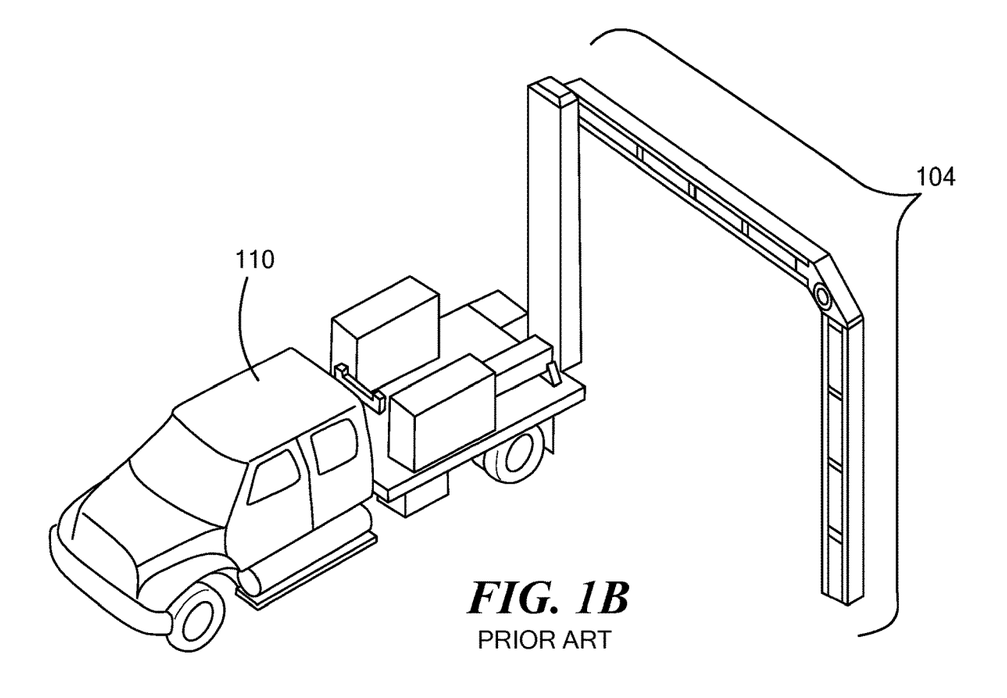
Figure 1C:
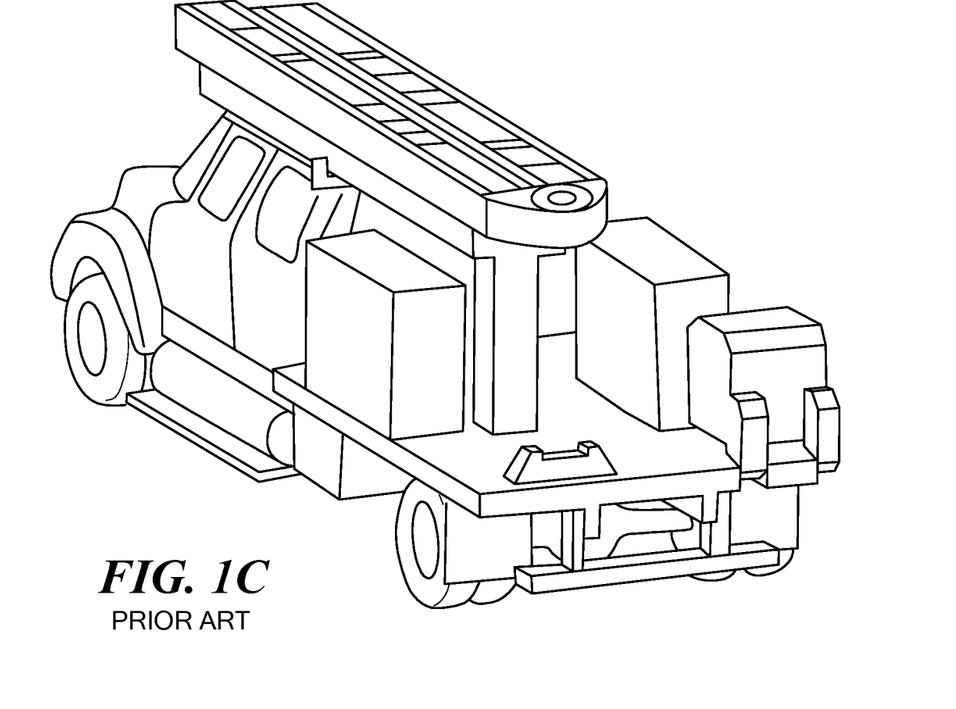
Figure 1D:
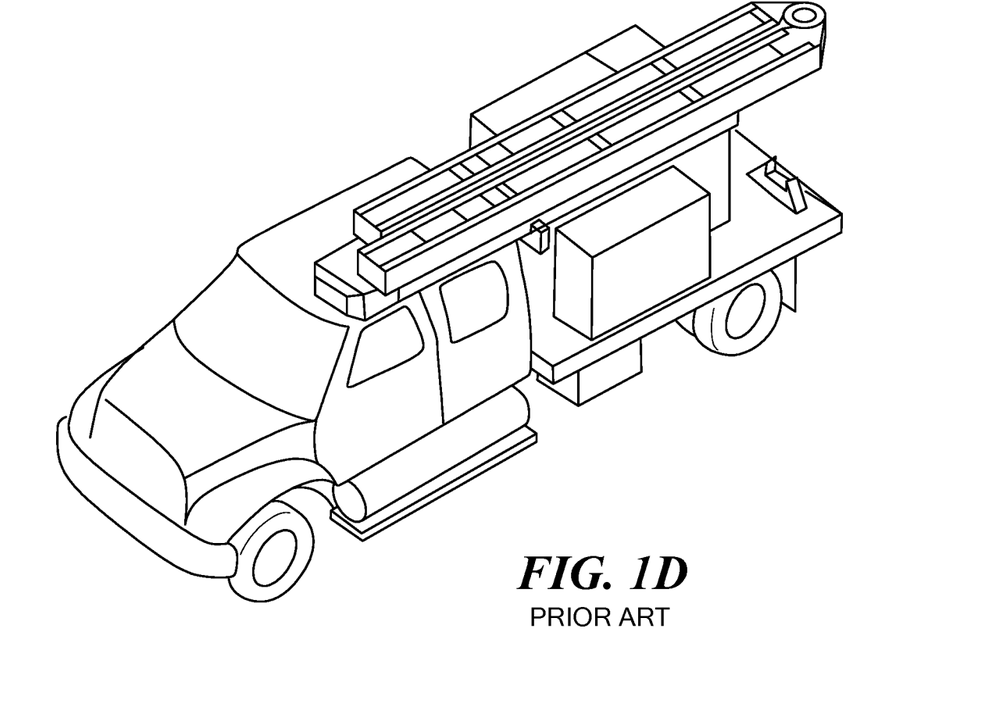

Source 106 emits penetrating radiation, typically x-rays, that are transmitted through inspected object 124 (otherwise referred to herein as a "target") and detected by the detector elements of detector array 104. Support of detector array 104 relative to conveyance 110 (otherwise referred to herein as a "moving platform" or an "inspection platform") is provided by boom 121 and mast 122, jointly comprising a structure that may be referred to herein as a "pontine structure." Boom 121 and mast 122 may be adapted for deployment during inspection operation, and stowed for on-road travel.

X-ray inspection system 100 is typically entirely integral with conveyance 110. Conveyance 110 may be a truck, capable of self-propulsion on, or off, roads, or conveyance 110 may also be a trailer that may be hauled by a truck or other self-propelled tractor. X-ray inspection system 100 may also be operated in a "portal" mode, where the system is stationary and inspected object 124 (which may be a vehicle, or a trailer) moves past it. In other cases, x-ray inspection system 100 may move past an inspected object.

Security inspection based on emission of x-rays from moving platform 110 and detection of x-rays traversing inspected object 124 is limited with respect to the speed of the moving platform 110 relative to the inspected object 124. Inspected object 124 may be a vehicle, for example. The reason for stringent speed requirements is that x-rays must dwell on each inspected cross-section of the target 124 for a duration of time that achieves an adequate ratio of signal to noise in the detected transmission signal. If the relative speed varies significantly, the sensitivity of detection will vary across regions of the inspected object, with faster scanning corresponding to lower sensitivity.

Therefore, motion of the inspection platform 110 must be governed in some manner, so as not to exceed a useful scanning speed. Prior art x-ray inspection systems 100 employed myriad design approaches. In some cases, the motion of inspection platform 110 was governed open-loop, with a driver required to maintain a specified scanning speed. In other cases, an independent motive system was added into or onto the inspection platform 110, typically a truck chassis. Examples have included counter-rotating drum systems that use friction applied to the truck tire, deployable systems that contacted the ground (tag axles, helper drives), drive shaft systems that rotated the vehicle's drive shaft with the transmission in neutral, or transfer case systems that interrupted the standard driveline with additional electric or hydraulic motors. Some of these systems used energy provided by the truck engine converted either by a power take-off (PTO) or through a transfer case. Other systems have been powered by electricity from an onboard generator or a shore power connection.

Unfortunately, each of the prior art systems for limiting scanning speed has its own drawbacks. These include reliance on driver judgment, complexity and attendant maintenance requirements, the requirement of additional external sources of power, and the need for finely-tuned control and feedback systems.

It would be advantageous to inspect vehicles without the complexity overhead of existing systems that are invariably employed to limit scanning speeds.

SUMMARY OF EMBODIMENTS OF THE INVENTION

In accordance with embodiments of the present invention, a conveyance is provided for x-ray transmission inspection. The conveyance, which may be adapted for autonomous or remotely controlled operation, has a bed having a longitudinal axis parallel to a direction of motion, with a plurality of wheels coupled to the bed. The conveyance also has a plurality of detector elements disposed along a pontine structure coupled to the conveyance and a source of penetrating radiation coupled to the conveyance and disposed so as to irradiate each of the detector elements from a single position. Finally, the conveyance has an automated manual transmission for coupling power from an engine to a set of the plurality of wheels both for road travel and for x-ray inspection operations.

In accordance with alternate embodiments of the present invention, the pontine structure may be adapted for deployment during inspection operation. The automated manual transmission may include a dual-clutch transmission.

In further embodiments, the conveyance may have a rear axle differential adapted to provide motion of the conveyance at a specified velocity. The conveyance may weigh less than 15 tons.

In accordance with other aspects of the present invention, methods are provided for inspecting an object, that have steps of irradiating, from a single position on a bed of a conveyance, each of a plurality of detector elements disposed along a pontine structure coupled to the conveyance, and coupling power, via an automated manual transmission, to a set of a plurality of wheels coupled to the conveyance, for road travel and for x-ray inspection operations.

In other embodiments of the invention, coupling power via the automated manual transmission may include coupling power via a dual-clutch transmission, and may also include coupling power to the set of the plurality of wheels via a rear axle differential adapted to provide motion of the conveyance at a specified velocity. Methods in accordance with the invention may also have a step of deploying the pontine structure from the conveyance for inspection operations.

BRIEF DESCRIPTION OF THE DRAWINGS

The foregoing features of the invention will be more readily understood by reference to the following detailed description, taken with reference to the accompanying drawings, in which.

DETAILED DESCRIPTION OF EMBODIMENTS OF THE INVENTION

Definitions

The term "set," as used herein, shall not include the empty set, and shall refer to any positive integer number $\{\subset \mathbf{C}\}$ of specified elements, including one. A set of elements may refer either to a subset of a collection of elements, or to the entirety of the collection of elements.

The term "plurality," as used herein, shall mean "two or more."

As used herein, the term "penetrating radiation" refers to electromagnetic radiation of sufficient energy per photon to penetrate materials of interest to a substantial and useful degree and include x-rays and more energetic forms of radiation. For convenience, the term "x-ray" may be used, without limitation, as an example of penetrating radiation as employed within the scope of the present invention.

The interaction of penetrating radiation with matter can generally be categorized as either scattering or absorption processes. Both types of process remove x-ray photons from a collimated (i.e., directional) beam; scattering processes do so by deflecting photons into new directions (usually with loss of energy), while absorption processes simply remove photons from the beam.

As a matter of heuristic convenience, orientational designations may be referred to herein, and in any appended claims, with respect to local surface features. Thus, for example, "horizontal" denotes a plane parallel to the bed of a truck parked on the ground, whether the local surface of the ground is rigorously horizontal or, itself, on a slope.

A "mobile platform" may refer to a truck, trailer or any other conveyance than can easily be moved to a new location. As used in this description and in the appended claims, a "vehicle" includes any conveyance that may be driven, pushed, or pulled from one place to another, whether over the surface of land or otherwise, including conveyances that operate under remote or autonomous control, where adapted to do so. The terms "vehicle," "conveyance," and "mobile platform," are synonymous for present purposes only, and, as used herein and in any appended claims, further include the structures, components and contents that are conveyed together with the respective conveyance.

"Pontine" means having the shape of a bridge, or "U-shaped."

As used in this description and in the appended claims, the term "image" refers to any multidimensional representation, whether in tangible or otherwise perceptible form or otherwise, whereby a value of some characteristic is associated with each of a plurality of locations corresponding to dimensional coordinates of an object in physical space, though not necessarily mapped one-to-one thereonto. Thus, for example, the graphic display of the spatial distribution of some feature, such as atomic number, in one or more colors constitutes an image. So, also, does an array of numbers in a computer memory or holographic medium. Similarly, "imaging" can refer to the rendering of a stated physical characteristic for visual inspection by a human.

Embodiments of the invention described herein serve to characterize materials which may be contained within an inspected vehicle, or an item of cargo, or a cargo container, and thus not readily susceptible to visual scrutiny. The characteristics of a material which might be the object of non-invasive inspection and which lend themselves to detection using the device and method taught by the invention include, but are not limited to, electron density, atomic number, mass density, linear dimensions and shape, as well as autonomous emission (such as due to fission or to radioactive decay). These characteristics are unveiled by taking advantage of the various physical processes by which penetrating radiation interacts with matter.

Figure 2:
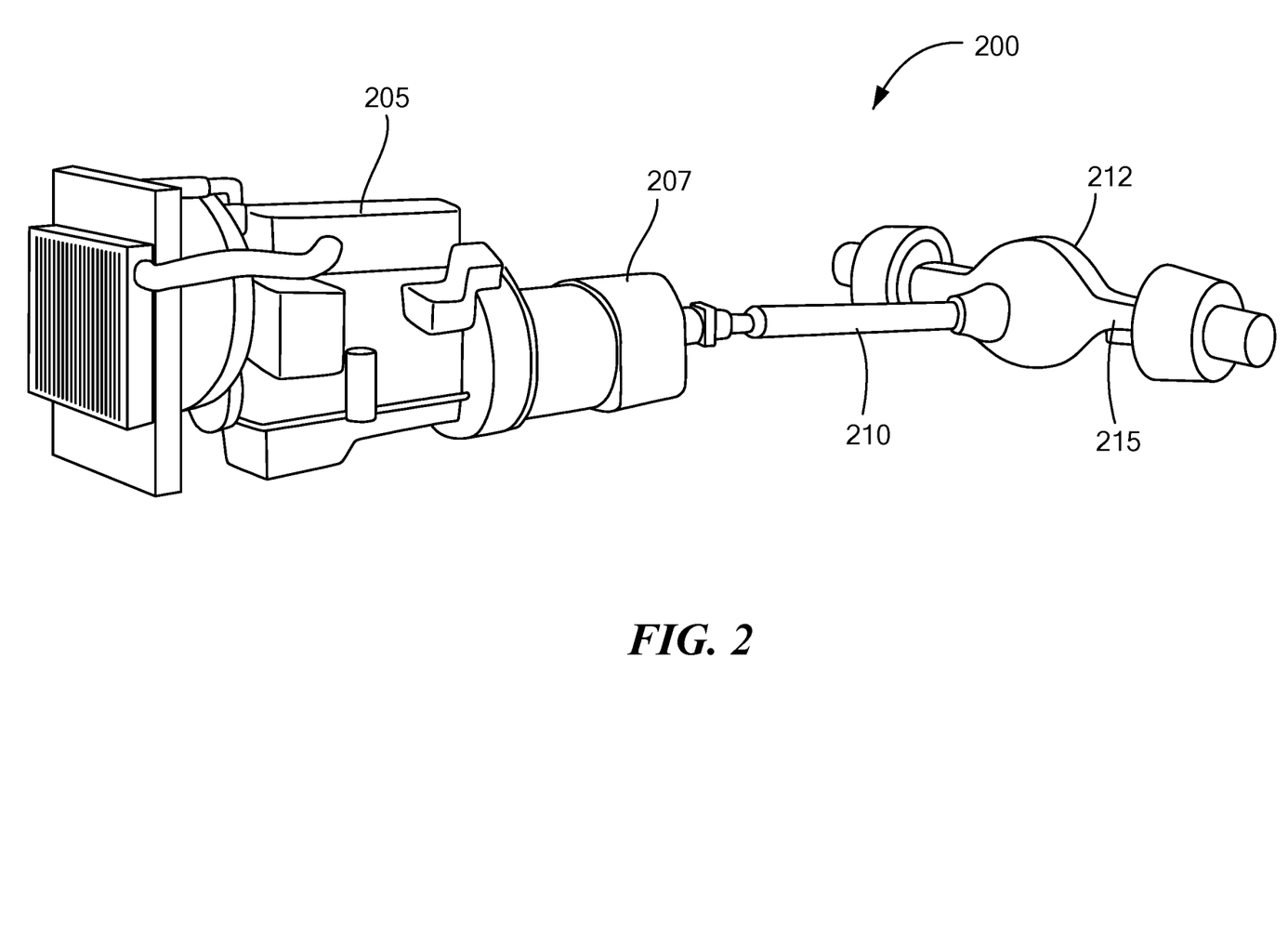
FIG. 2 depicts a perspective view of a prior art engine and drive train.

The general layout of the drivetrain 200 of a heavy-duty automotive engine is shown in FIG. 2, depicting engine 205, transmission 207, driveshaft 210, rear differential 212 and rear axle 215.

Figure 3:
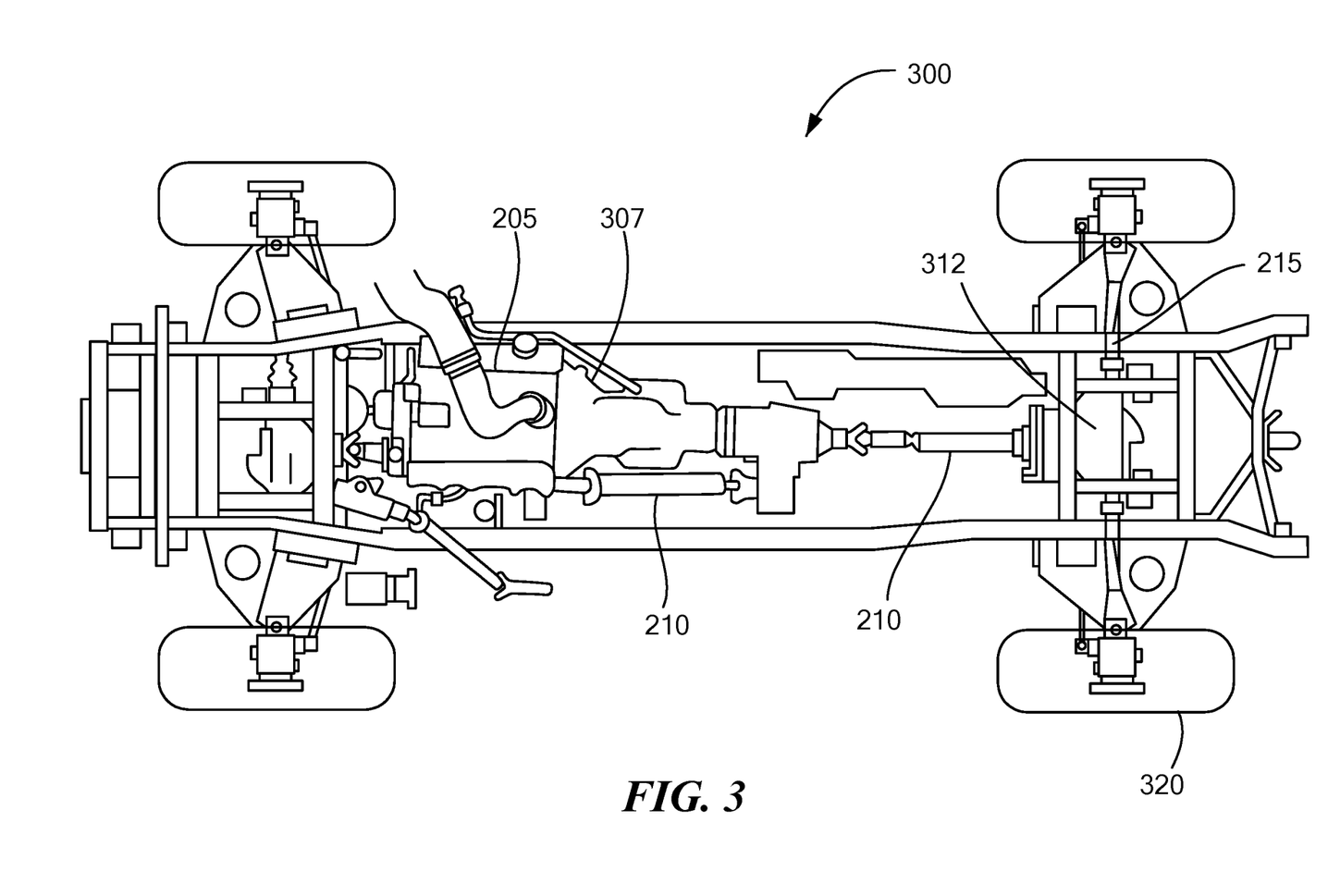
FIG. 3 depicts a schematic cross section of a prior art engine and drive train, parallel to the chassis of an inspection vehicle.

In accordance with embodiments of the present invention, an automated manual transmission system 307 is employed to provide precise, slow-speed motion to translate x-ray inspection system 100 (shown in FIG. 1) past an inspected object 124 (shown in FIG. 1), as now described with reference to FIG. 3. Inspected object 124 may be a vehicle, a cargo container, for example, or any other matter subject to x-ray inspection, and may be referred to herein simply as an "object." FIG. 3 depicts the elements of a drivetrain 300 of a heavy-duty automotive engine of an inspection vehicle 401 (shown in FIG. 4) in a cross sectional schematic. An automated manual transmission (AMT) system 307, for purposes of the present description and any appended claims, shall refer to any transmission that performs a clutch operation smoothly engaging a succession of gears without the intervention of a driver. This is accomplished by means of sensors and a central processor that determines a timing and torque requisite for smooth clutch engagement. AMT systems are available commercially for application in heavy-duty automotive applications from such vendors as Eaton Corp. of Cleveland, Ohio. Any number of wheels (constituting a "set" of the wheels of a conveyance) may be driven, within the scope of the present invention. AMT systems combine a manual-shift medium duty truck transmission with automated clutching, gear selection mechanisms and computer control. Some units make use of a "dual clutch" technology to enable more seamless changes in gears. AMT systems are not standard equipment on vehicles capable of carrying x-ray inspection systems, which is to say, medium-duty trucks in the range below 15 gross tons. AMT systems differ from typical automatic transmissions in that they do not use a fluid-coupling torque converter between the engine and transmission. As a result, there is a fixed low-speed gear ratio while the vehicle accelerates.

Figure 4:
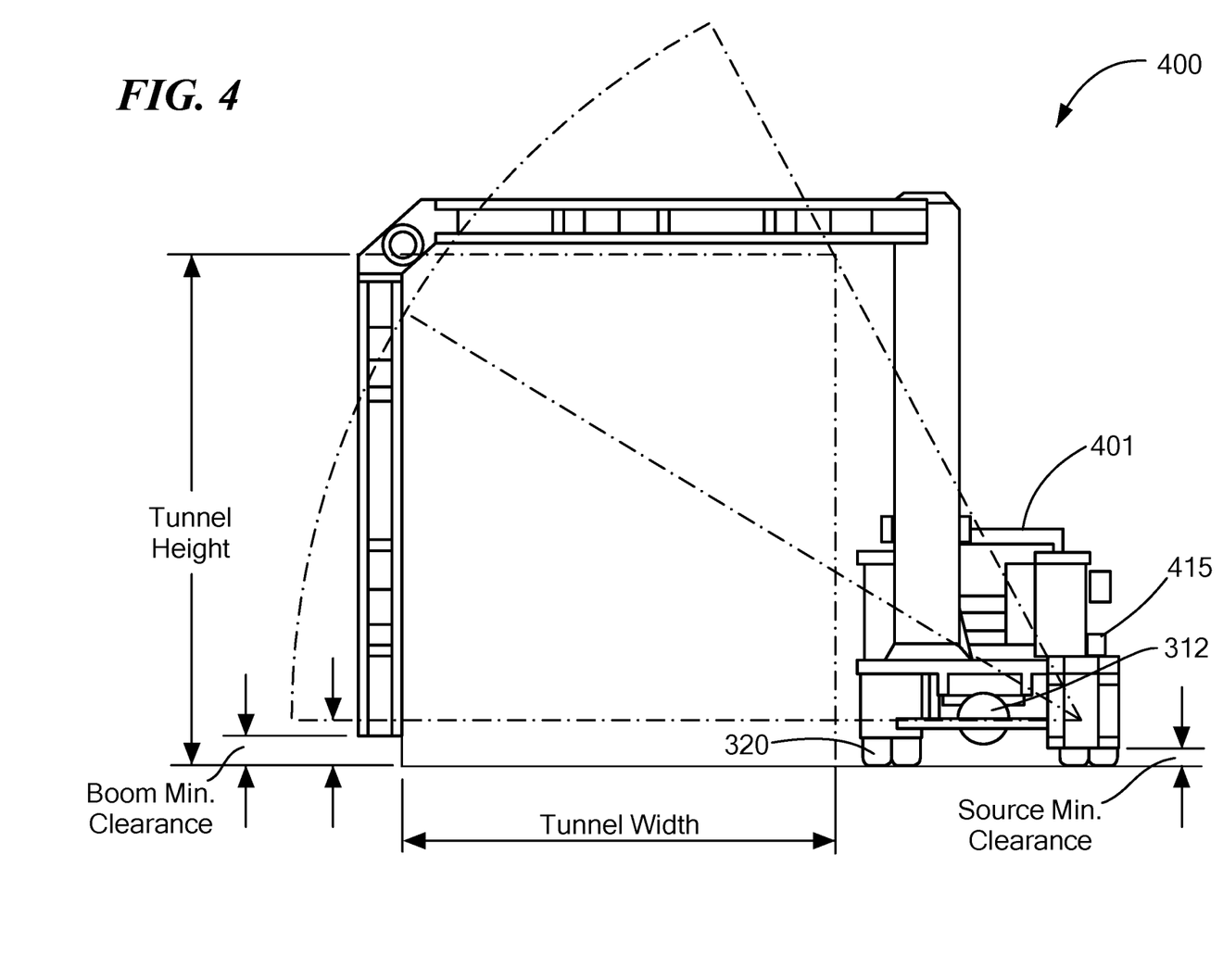
FIG. 4 depicts a cross section of an x-ray inspection vehicle employing an automated manual transmission, in accordance with an embodiment of the present invention.

The AMT system 307 is used in combination with gear ratios in the rear axle differential 312 (i.e., the "final drive" ratio) and a sizing of tires 320 adapted to allow the inspection vehicle 401 to move at a specified scan speed when running at low engine RPM. FIG. 4 shows an x-ray inspection system 400 incorporating inspection vehicle 401 that incorporates an AMT system 307 and a the rear axle differential 312 adapted, in conjunction with tires 320, to allow the inspection vehicle 401 (also referred to herein as a "truck") to move at a specified scan speed when running at a low rate of engine revolutions per minute (RPM). An x-ray inspection system is mounted on a bed 415 characterized by a direction of motion into the page. Inspection vehicle 401 may be operated at idle, in some modes of operation, and at other engine rates, in other modes of operation. No additional system is required for achieving the desired functionality, and all motive power is derived directly from the engine 205 (otherwise referred to as the "chassis engine").

AMT system 307 may advantageously enable a "creep mode" feature in a medium-duty truck transmission. This feature holds a transmission in a specified gear and allows the truck to creep at engine idle speed. Previously this feature was made available on larger transmissions to aid semi-trailer truck drivers to maneuver in the confines of a loading dock without worrying about gear selection and stalling.

X-ray inspection vehicles in the prior art that used x-rays of greater than 250 keV in transmission were large systems weighing up to and greater than 50,000 lbs. Therefore, AMT systems could never possibly have been used on such prior art systems. Only now, as a new market segment has developed around vehicles weighing 26,000 lbs or less, which can be driven with a standard US license (i.e. non-CDL drivers), is it possible, for the first time, to ever consider the use of an AMT system. Moreover, only newer engines, with sufficient low end torque, appropriate engine RPM regimes and emissions controls, have made it possible for a customer to use the vehicle all day at idle speeds without the needing to switch to a smaller diesel generator in order to limit emissions.

Moreover, typical scan speeds were previously as low as 0.2-0.4 m/s, a range in which operation of an AMT in creep mode would be totally impossible. Only with the improvement of imaging technology to meet heightened throughput requirements has it become possible to operate inspection vehicles at scan speeds near 1 m/s (2 mph) where use of an AMT becomes possible for the first time.

In accordance with further embodiments of the present invention, two speed rear axles may be employed. The ability to shift between high and low final drive ratios is useful (but not necessary) to achieve the high reduction required for this scan drive approach. Manufacturers do not currently make two speed rear axles in the weight rating typical for 26,000 lb vehicles, but equipment designed for heavier trucks can be adapted to these chasses.

Example drive speed calculations showing how variability of a final drive ratio (including two-speed rear axle) and tire size affects the speed of the vehicle, both at engine idle (750-800 RPM) and at highway speed (2600 RPM), are presented in the following table:

In accordance with aspects of the present invention, x-ray inspection may proceed in the following manner:

The driver (not shown) arranges the targets 124 (shown in FIG. 1) to be scanned, deploy the imaging system and align the truck 401 (transmission in "Drive") per standard practice.

With the vehicle 401 stopped and the brake pedal depressed, the driver selects the lowest gear of the transmission (done via a user interface 500—shown in FIG. 5, and otherwise referred to herein as a "keypad shift console") and selects the "creep drive" transmission function—a function that will hold the selected gear and enable the transmission programming. In some embodiments, selection of the lowest gear may be the default behavior for the transmission and does not need user activation.

The driver releases the brakes, and depresses the accelerator only enough (if at all) to get the vehicle moving and allow the clutch to fully engage.

The driver releases the accelerator, and the transmission will remain in gear, moving the vehicle at engine idle speed. The correct final speed (typically, 2 mph, for example) is maintained via selection of the final drive ratios and tire size of the vehicle.

When the scan is complete, the driver steps on the brakes to stop the truck 401, and can then put the transmission back into "Drive" and move the vehicle as necessary.

Advantages of operation in accordance with precepts of the present invention include safety of operation, in that the driver need only rely on the instinctual controls of the vehicle—steering wheel, brake pedal, accelerator. Additionally, by elimination a second drive system, robustness and reliability may advantageously be increased, costs may be lowered. Moreover, the system may weigh less and have fewer maintenance requirements.

Furthermore, in accordance with embodiments of the present invention, engine 205 will drive the truck without additional generator power, or the need to convert energy via a power takeoff (PTO) or transfer case. And, whereas fine-tuning the motion control and feedback systems as in typical scan drives is a difficult control systems problem, a system in accordance with the present invention relies on the low-complexity, high-precision electronic ignition system of the vehicle chassis to maintain a fixed engine RPM. In this system the rotating inertia of the engine, driveline and vehicle momentum help stabilize the drive speed, rather than hinder it.

Figure 5:
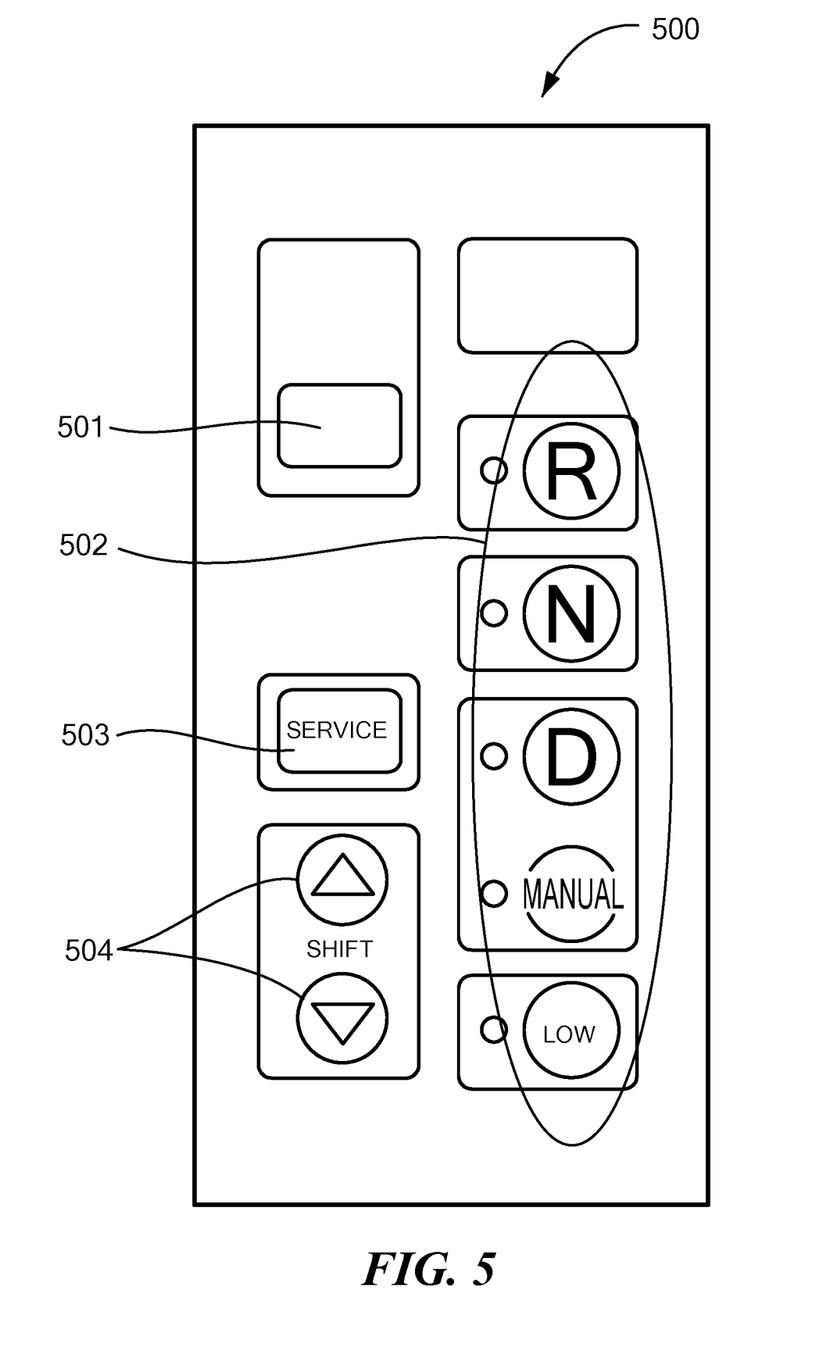
FIG. 5 shows a prior art keypad-type shift console, for use with an automated manual transmission.

User interface 500, shown, in one embodiment, in FIG. 5, is any structure, otherwise denoted a "gear shift," which allows a driver or other user to control operation of an automated manual transmission in accordance with embodiments of the present invention. Manual gear selection buttons 504 allow shifting between gear settings shown by gear

|  |  | Transmission & Final Drive Config A | | | Config B (2-Speed Rear Axle) | | |
| --- | --- | --- | --- | --- | --- | --- | --- |
|  |  | 1st | 7th | Reverse | 1st | 7th | Reverse |
| Engine RPM | RPM | 750 | 2600 | 750 | 800 | 2600 | 800 |
| Transmission Gear Ratio | X:1 | 6.5 | 0.64 | −6.15 | 6.5 | 0.64 | −6.15 |
| Differential Ratio | X:1 | 6.14 | 6.14 | 6.14 | 7.6 | 5.57 | 7.6 |
| Tire Speed | RPM | 18.8 | 661.6 | −19.9 | 16.2 | 729.4 | −17.1 |
| Tire SLR | in | 17.5 | 17.5 | 17.5 | 19 | 19 | 19 |
| Tire Circumference | in | 110.0 | 110.0 | 110.0 | 119.4 | 119.4 | 119.4 |
| Final Speed | mph | 2.0 | 68.9 | −2.1 | 1.8 | 82.5 | −1.9 | selection indicator lamps 502. A service indicator lamp 503 and a power takeoff (PTO) indicator lamp 501 may also be provided.

The described embodiments of the invention are intended to be merely exemplary and numerous variations and modifications will be apparent to those skilled in the art. All such variations and modifications are intended to be within the scope of the present invention as defined in the appended claims.

I claim:

1. A conveyance for X-ray inspection of an object, the conveyance comprising:
   a bed having a longitudinal axis parallel to a direction of motion;
   a plurality of wheels coupled to the bed;
   a plurality of detector elements disposed along a pontine structure coupled to the conveyance;
   a source of penetrating radiation coupled to the conveyance and disposed so as to irradiate each of the detector elements from a single position; and
   an automated manual transmission for coupling power from an engine to a set of the plurality of wheels both for road travel and for X-ray inspection operations.

2. The conveyance in accordance with claim 1, wherein the conveyance is adapted for operation under autonomous control.

3. The conveyance in accordance with claim 1, wherein the pontine structure is adapted for deployment during inspection operation.

4. The conveyance in accordance with claim 1, wherein the automated manual transmission includes a dual-clutch transmission.

5. The conveyance in accordance with claim 1, further comprising a rear axle differential adapted to provide motion of the conveyance at a specified velocity.

6. The conveyance in accordance with claim 1, wherein the conveyance weighs less than 15 tons.

7. A method for inspecting an object, the method comprising:
   irradiating, from a single position on a bed of a conveyance, the conveyance having a plurality of wheels, each of a plurality of detector elements disposed along a pontine structure coupled to the conveyance; and
   coupling power via an automated manual transmission to a set of the plurality of wheels of the conveyance for road travel and for X-ray inspection operations.

8. The method in accordance with claim 7, wherein coupling power via the automated manual transmission includes coupling power to the set of the plurality of wheels via a dual-clutch transmission.

9. The method in accordance with claim 7, wherein coupling power via the automated manual transmission includes coupling power to the set of the plurality of wheels via a rear axle differential adapted to provide motion of the conveyance at a specified velocity.

10. The method in accordance with claim 7, further comprising deploying the pontine structure from the conveyance for inspection operations.

11. A conveyance for X-ray inspection of an object, the conveyance comprising:
    a bed having a longitudinal axis parallel to a direction of motion;
    a plurality of wheels coupled to the bed;
    a plurality of detector elements disposed along a U-shaped structure coupled to the conveyance;
    a source of penetrating radiation coupled to the conveyance and disposed so as to irradiate each of the detector elements from a single position; and
    a transmission configured to perform a clutch operation that engages a succession of gears without an intervention by a driver, wherein the transmission is adapted to couple power from an engine to a set of the plurality of wheels both for road travel and for X-ray inspection operations.

12. The conveyance in accordance with claim 11, wherein the conveyance is adapted for operation under autonomous control.

13. The conveyance in accordance with claim 11, wherein the U-shaped structure is adapted for deployment during inspection operation.

14. The conveyance in accordance with claim 11, wherein the transmission includes a dual-clutch transmission.

15. The conveyance in accordance with claim 11, further comprising a rear axle differential adapted to provide motion of the conveyance at a specified velocity.

16. The conveyance in accordance with claim 11, wherein the conveyance weighs less than 15 tons.

17. A method for inspecting an object, the method comprising:
    irradiating, from a single position on a bed of a conveyance, the conveyance having a plurality of wheels, each of a plurality of detector elements disposed along a U-shaped structure coupled to the conveyance; and
    coupling power via a transmission configured to perform a clutch operation that engages a succession of gears without an intervention by a driver to at least some of the plurality of wheels of the conveyance for road travel and for X-ray inspection operations.

18. The method in accordance with claim 17, wherein coupling power via the transmission includes coupling power to the set of the plurality of wheels via a dual-clutch transmission.

19. The method in accordance with claim 17, wherein coupling power via the transmission includes coupling power to the set of the plurality of wheels via a rear axle differential adapted to provide motion of the conveyance at a specified velocity.

20. The method in accordance with claim 17, further comprising deploying the U-shaped structure from the conveyance for inspection operations.

21. A conveyance for X-ray inspection of an object, the conveyance comprising:
    a bed having a longitudinal axis parallel to a direction of motion;
    a plurality of wheels coupled to the bed;
    a plurality of detector elements disposed along a bridge shaped structure coupled to the conveyance;
    a source of penetrating radiation coupled to the conveyance and disposed so as to irradiate each of the detector elements from a single position; and
    a transmission configured to perform a clutch operation that engages a succession of gears without an intervention by a driver, wherein the transmission is adapted to couple power from an engine to a set of the plurality of wheels both for road travel and for X-ray inspection operations.

22. The conveyance in accordance with claim 21, wherein the conveyance is adapted for operation under autonomous control.

23. The conveyance in accordance with claim 21, wherein the bridge shaped structure is adapted for deployment during inspection operation.

24. The conveyance in accordance with claim 21, wherein the transmission includes a dual-clutch transmission.

25. The conveyance in accordance with claim 21, further comprising a rear axle differential adapted to provide motion of the conveyance at a specified velocity.

26. The conveyance in accordance with claim 21, wherein the conveyance weighs less than 15 tons.

27. A method for inspecting an object, the method comprising:
- irradiating, from a single position on a bed of a conveyance, the conveyance having a plurality of wheels, each of a plurality of detector elements disposed along a bridge shaped structure coupled to the conveyance; and
- coupling power via a transmission configured to perform a clutch operation that engages a succession of gears without an intervention by a driver to at least some of the plurality of wheels of the conveyance for road travel and for X-ray inspection operations.

28. The method in accordance with claim 27, wherein coupling power via the transmission includes coupling power to the set of the plurality of wheels via a dual-clutch transmission.

29. The method in accordance with claim 27, wherein coupling power via the transmission includes coupling power to the set of the plurality of wheels via a rear axle differential adapted to provide motion of the conveyance at a specified velocity.

30. The method in accordance with claim 27, further comprising deploying the bridge shaped structure from the conveyance for inspection operations.

* * * * *